(12) United States Patent
Krause et al.

(10) Patent No.: US 10,543,151 B2
(45) Date of Patent: Jan. 28, 2020

(54) QUICK CHANGE I.V. INTERFACE TECHNOLOGY

(71) Applicants: Jason G. Krause, Wausau, WI (US); John Harmon, Spring Valley, WI (US)

(72) Inventors: Jason G. Krause, Wausau, WI (US); John Harmon, Spring Valley, WI (US)

(73) Assignee: Krause Dairy Products, LLC, Pleasant Grove, UT (US)

( * ) Notice: Subject to any disclaimer, the term of this patent is extended or adjusted under 35 U.S.C. 154(b) by 798 days.

(21) Appl. No.: 13/751,953

(22) Filed: Jan. 28, 2013

(65) Prior Publication Data
US 2014/0034186 A1 Feb. 6, 2014

Related U.S. Application Data

(60) Provisional application No. 61/590,981, filed on Jan. 26, 2012.

(51) Int. Cl.
*A61M 5/30* (2006.01)
*A61J 1/20* (2006.01)
(Continued)

(52) U.S. Cl.
CPC .............. *A61J 1/2089* (2013.01); *A61M 5/30* (2013.01)

(58) Field of Classification Search
CPC .......... A61M 5/30; A61M 37/00; A61M 5/32; B67D 7/60; B65D 5/72
See application file for complete search history.

(56) References Cited

U.S. PATENT DOCUMENTS 4,969,883 A * 11/1990 Gilbert et al. ................ 604/414
6,485,472 B1 * 11/2002 Richmond .................... 604/246

FOREIGN PATENT DOCUMENTS

EP 0527951 * 7/1991

OTHER PUBLICATIONS

SyrVet (TM), US 2010.*
Random House Kernerman Webster's College Dictionary, 2005.*

* cited by examiner

*Primary Examiner* — Tatyana Zalukaeva
*Assistant Examiner* — Ilya Y Treyger
(74) *Attorney, Agent, or Firm* — Skinner and Associates; Joel Skinner

(57) ABSTRACT

A quick change adapter and method for use in intravenous treatment of large animals such as cattle, horses, pigs, goats and the like. A method for changing bottles of fluids used in intravenous (IV) fluid therapy, includes the steps of (a) providing an IV set including a funnel having a connection aperture, the funnel being constructed of elastic material; (b) providing an adapter apparatus comprising a cannular portion adapted for sealing mating with the fluid egress aperture of a fluid bottle and a lip portion adapted for sealing mating with the funnel aperture; (c) coupling the interface apparatus in a semi-permanent fashion to the funnel by inserting the lip portion into the funnel connection aperture; (d) inserting the cannular portion into the fluid egress aperture of the fluid bottle; and (e) inverting the fluid bottle to facilitate the flow of fluid. The adapter for connecting an IV Set to a bottle containing fluid, the IV Set of the type having a flexible funnel with a female-type connection aperture, includes a generally cylindrical body with a fluid flow lumen, the body having a lip disposed at one end adapted for male-type connection to the IV Set connection aperture, the opposing end of the body being adapted for male-type insertion into the fluid egress aperture of the bottle.

5 Claims, 5 Drawing Sheets

(51) Int. Cl.
*A61M 37/00* (2006.01)
*A61M 5/32* (2006.01)
*B67D 7/60* (2010.01)

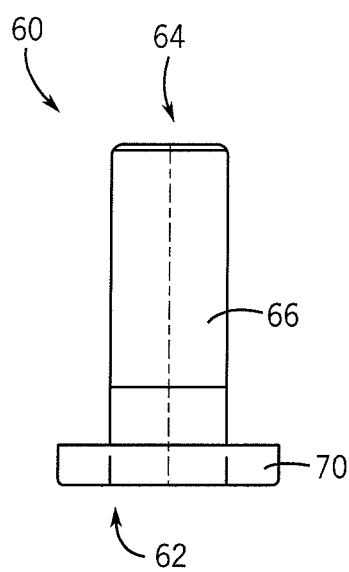 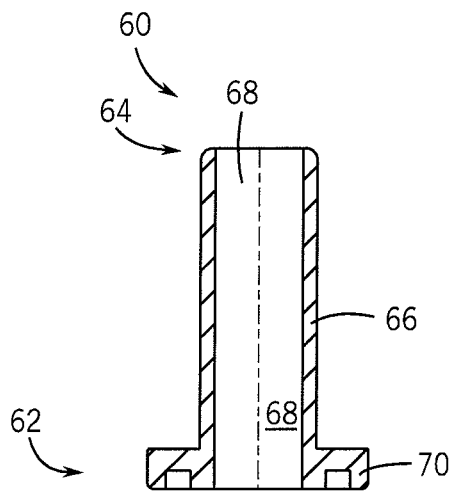 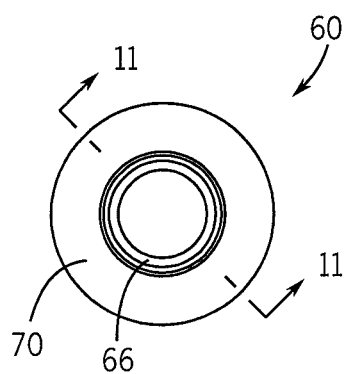 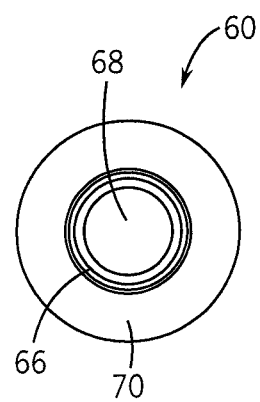 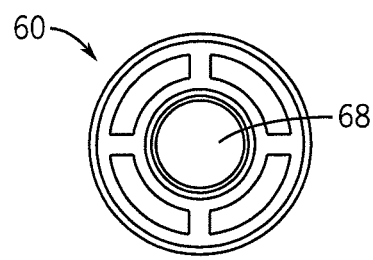

QUICK CHANGE I.V. INTERFACE TECHNOLOGY

CROSS REFERENCE TO RELATED APPLICATIONS, IF ANY

This application claims the benefit under 35 U.S.C. § 119(e) of U.S. Provisional Patent Application Ser. No. 61/590,981, filed Jan. 26, 2012, which is hereby incorporated by reference.

37 C.F.R. § 1.71(E) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

Field of the Invention

The present invention relates, generally, to veterinary medical and animal health devices, methods and systems. Particularly, the invention relates to an adapter and method of use therefore to be used by veterinarians, veterinary technologists and technicians, and herdsmen for administering fluids and medicaments rapidly and repeatedly to animals via intravenous (I.V.) injection. The apparatus and methods of the invention are most particularly useful for rapid, repeatable IV fluid administration and therapy for large animals such as cattle, horses, pigs, goats and the like.

Background Information

Animal husbandry has been a part of human life since the dawn of civilization. Veterinary medicine has evolved as a means for taking care of animals important to our economy. In particular, the health and well-being of large animals such as cows, horses, pigs, goats and the like is important. With respect to bovine, dairy farms and ranches exist throughout the world. Many dairy farms are now mega-farms with thousands of cattle, and with less and less personnel to care for sick animals and to maintain healthy animals.

Many times veterinary procedures and treatments are needed to care for these animals. Such treatments include intravenous (IV) injections of compositions, including medicaments such as antibiotics, and other fluids such as rehydration solutions, electrolyte balance control solutions, trace mineral, vitamin, and nutritional supplement solutions. Because bovine are such large creatures, a source of treatment may include several doses of medication or fluids depending upon body weight and condition of the animal. For example, a treatment for mineral deficiencies may call for 500 ml per 400 kilograms of body weight. Bovine medicaments and fluids are commonly provided in Five Hundred Milliliter (500 ml.) bottles. Such bottles are typically made of plastic and have a cylindrical container portion with a lower diameter cylindrical neck terminating in a flange that has a larger diameter than the neck. For IV administration, such bottles are typically connected to an intravenous fluid administration set (IV set) called a Simplex IV Set. In the case of large animals such as cattle, treatment may necessitate several 500 ml bottles applied intravenously to each animal. And, often several animals are treated at the same time. This is a cumbersome, time consuming and messy operation with expensive fluids, all too often, being spilled and wasted as the Simplex IV Set is mated with a bottle, removed from the empty bottle and then reattached to a new bottle in a continuing process.

The Simplex IV set typically has a proximal funnel which connects to the flange and neck of the bottle of solution, a length of flexible tubing, a flow regulating devices such as a clamp connected to the tube, and a distal needle adapter and needle. The funnel has a seal portion and an air vent for regulating pressure and release of air pockets or bubbles in the fluid. The funnel is typically made of flexible silicone based plastic material and is designed to stretch and fit over the top flange or lip of the bottle. The inside diameter of the seal portion of the funnel is designed to be smaller than the lip diameter of the bottle with a taper above the seal portion to assure a tight fit. However, a problem exists in that the tapered configuration and tight fit, especially when coupled with the properties of the surgical tubing, is extremely difficult to maneuver over the lip of the bottle. This difficult manipulations is exacerbated in light of the distractions typically found in a veterinary or livestock setting. This process must be repeated for each bottle of fluid administered. And the process may sometimes be repeated for plural animals.

Therefore, it would be advantageous to provide a quick change interface or adapter between the I.V. Set and the bottle and a method of using the adapter to interface the IV Set and bottle and to swap new bottles for empty bottles.

In one aspect, the invention provides a method for changing bottles of fluids used in intravenous (IV) fluid therapy, comprising:

(a) providing an IV set including a funnel having a connection aperture, the funnel being constructed of elastic material;

(b) providing an adapter apparatus comprising a cannular portion adapted for sealing mating with the fluid egress aperture of a fluid bottle and a lip portion adapted for sealing mating with the funnel aperture;

(c) coupling the interface apparatus in a semi-permanent fashion to the funnel by inserting the lip portion into the funnel connection aperture;

(d) inserting the cannular portion into the fluid egress aperture of the fluid bottle; and (e) inverting the fluid bottle to facilitate the flow of fluid.

In another aspect the invention provides an adapter for connecting an IV Set to a bottle containing fluid, the IV Set being of the type having a flexible funnel with a female-type connection aperture, comprising a generally cylindrical body with a fluid flow lumen, the body having a lip disposed at one end adapted for male-type connection to the IV Set connection aperture, the opposing end of the body being adapted for male-type insertion into the fluid egress aperture of the bottle.

In yet another aspect the invention provides an apparatus for administering intravenous (IV) fluid therapy to large animals, comprising:

(a) a plurality of bottles of IV fluid;

(b) an IV Set including a flexible funnel with a female-type connection aperture, comprising a generally cylindrical body with a fluid flow lumen, the body having a lip disposed at one end adapted for male-type connection to the IV Set connection aperture, the opposing end of the body being adapted for male-type insertion into the fluid egress aperture of the bottle; and (c) An adapter for connecting an IV Set to a bottle containing fluid, the IV Set being of the type having a flexible funnel with a female-type connection aperture, comprising a generally cylindrical body with a fluid flow lumen, the body having a lip disposed at one end adapted for male-type connection to the IV Set connection aperture, the opposing end of the body being adapted for male-type insertion into the fluid egress aperture of the bottle.

BRIEF SUMMARY OF THE INVENTION

The present invention provides IV fluid administration apparatus and methods which are practical, reliable, safe, and efficient, and which are believed to constitute an improvement over the background technology.

The invention provides an adapter apparatus and a method of use therefore which efficiently and quickly transfers a Simplex IV Set from one bottle of veterinary medical fluid (solutions and medicaments) to a second bottle during the IV Fluid Therapy for animals, particularly large animals such as cattle, horses and the like. A first end of the adapter is insertable into o the inside (female-type portion) of a Simplex IV Set Funnel. The second end of the adapter protrudes from the funnel and is insertable into the inside (female-type portion) of a IV Fluid bottle. Both ends form a fluid tight seal with the funnel and bottle apertures respectively. The second end of the adapter is quickly disconnectable from the bottle upon being emptied of fluid. The second end can then be inserted into a new full bottle of fluid. The adapter and method of use obviates the need to stretch and friction fit the Simplex Funnel over the outside of the bottle lip/mouth. One adapter adapts to a range bottle neck sizes ranging from 28-33 mm. And the adapter is attachable to either a rubber or plastic type Simplex funnel. In summary, the adapter and method provide a quick, easy transfer of bottles to a Simplex IV set, little or no interruption of fluid flow occurs, little or no spilling of fluid occurs, less stress of the animal occurs, and the user can accomplish more work faster with less frustration. The adapter is reusable and economical to manufacture and to use.

The present invention is believed to involve novel elements, combined in novel ways to yield more than predictable results. The problems solved by the invention were not fully recognized in the prior art.

The aspects, features, advantages, benefits and objects of the invention will become clear to those skilled in the art by reference to the following description, claims and drawings.

BRIEF DESCRIPTION OF THE SEVERAL VIEWS OF THE DRAWING

The present invention, and the manner and process of making and using it, will be better understood by those skilled in the art by reference to the following drawings.

FIG. 8 is a side view of a second embodiment of the quick connect adapter of the present invention.

FIG. 9 is a first end view of the adapter.

FIG. 10 is an opposing, second end, view of the adapter.

FIG. 11 is a crossectional view of the adapter taken along line 11-11 of FIG. 9.

FIG. 12 is a detailed view of the adapter showing a means of labeling the adapter.

DETAILED DESCRIPTION

The invention provides a device, system and method of use therefore to be used by veterinarians, veterinary technologists and technicians, and herdsmen for administering fluids and medicaments rapidly and repeatedly to animals via intravenous (I.V.) injection. The apparatus and methods of the invention are most particularly useful for rapid, repeatable IV fluid administration and therapy for large animals such as cattle, horses, pigs, goats and the like.

Figure 1:
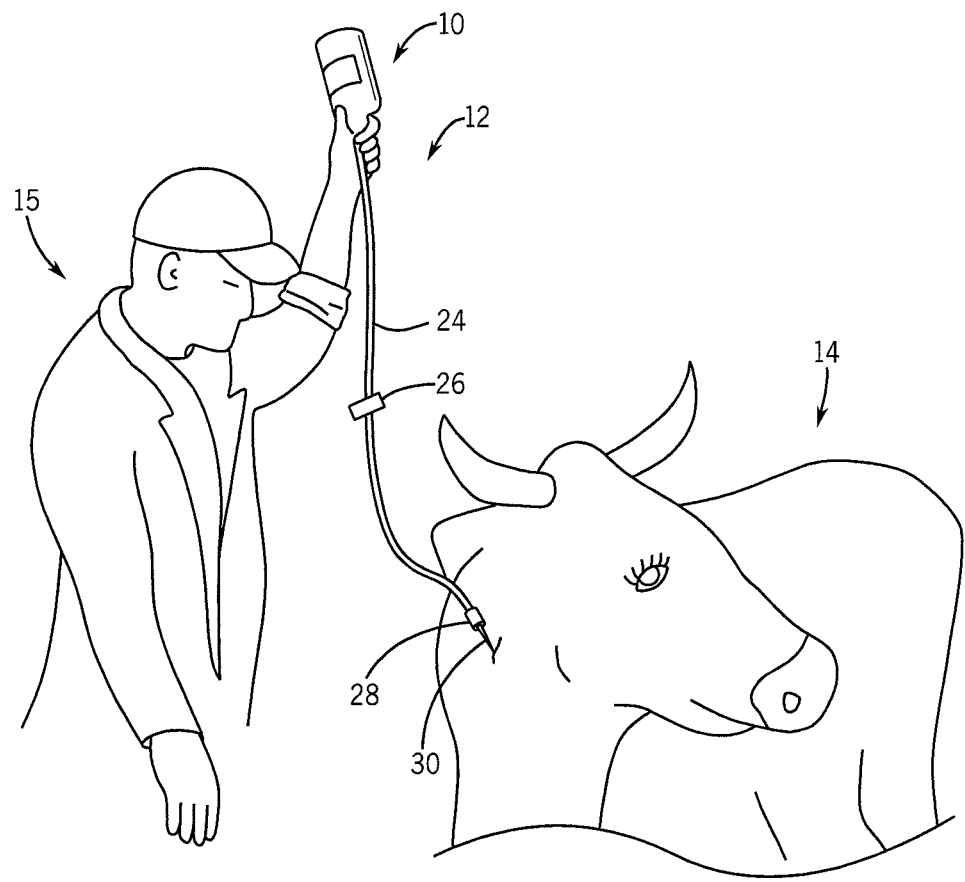
FIG. 1 illustrates a typical method of administering a fluid such as a medicament or a hydration solution intravenously (I.V. or IV) to a bovine using an IV Set and a 500 ml bottle.
Figure 2:
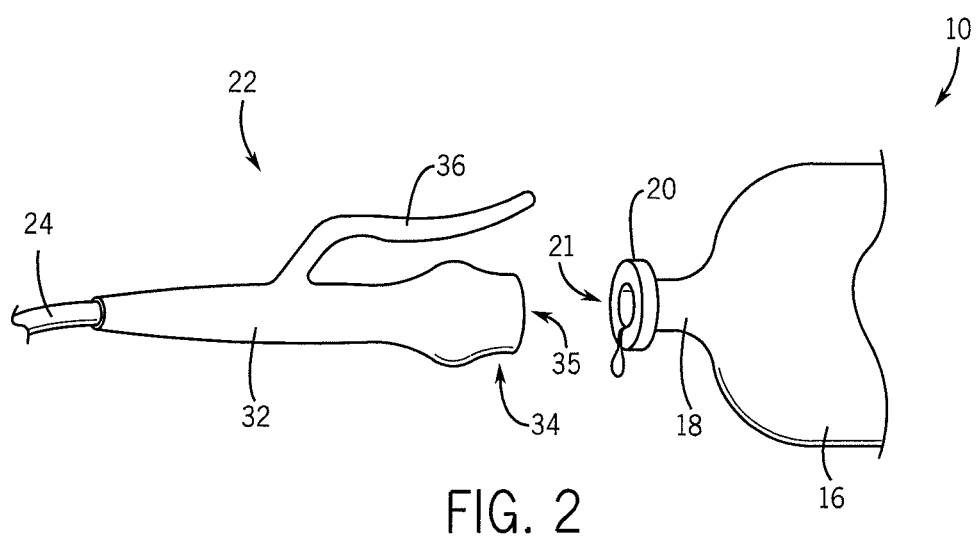
FIG. 2 illustrates a known, common method of connecting a common IV set to a fluid bottle via an IV Set funnel (with air vent and tubing) oriented for connection to the lip of the bottle.

Referring to FIG. 1, a medicaments and fluids are administered to cattle and other large animals intravenously via a container 10 connected to an Intravenous Fluid Administration Set (IV Set) 12 which has a needle which is injected into the cattle 14, for example at the jugular vein. The entire assembly of elements is shown held by a user 15, but it may be supported by a frame, stand or other holder. Referring also to FIG. 2, The container 10 is commonly a Five Hundred Milliliter (500 ml.) bottle. Such bottles are typically made of plastic and have a cylindrical container portion 16 with a lower diameter cylindrical neck 18 terminating in a flange 20 (also called a lip or neck finish) that has a larger diameter than the neck 18 and surrounds the egress aperture 21 of the bottle 10. Flanges 20 typically have a diameter of 28-33 mm (1.10-1.29 inches). During one fluid therapy session, a user 15 may encounter bottles of different sizes. The bottle lip or flange is covered with a seal or cap when new. Typical IV Fluid solutions for cattle include Calcium Gluconate, Electrolytes, and other hydration or nutritional fluid solutions, and medicament solutions such as antibiotics, either alone or in combination with hydration and/or nutritional compositions.

Figure 13:
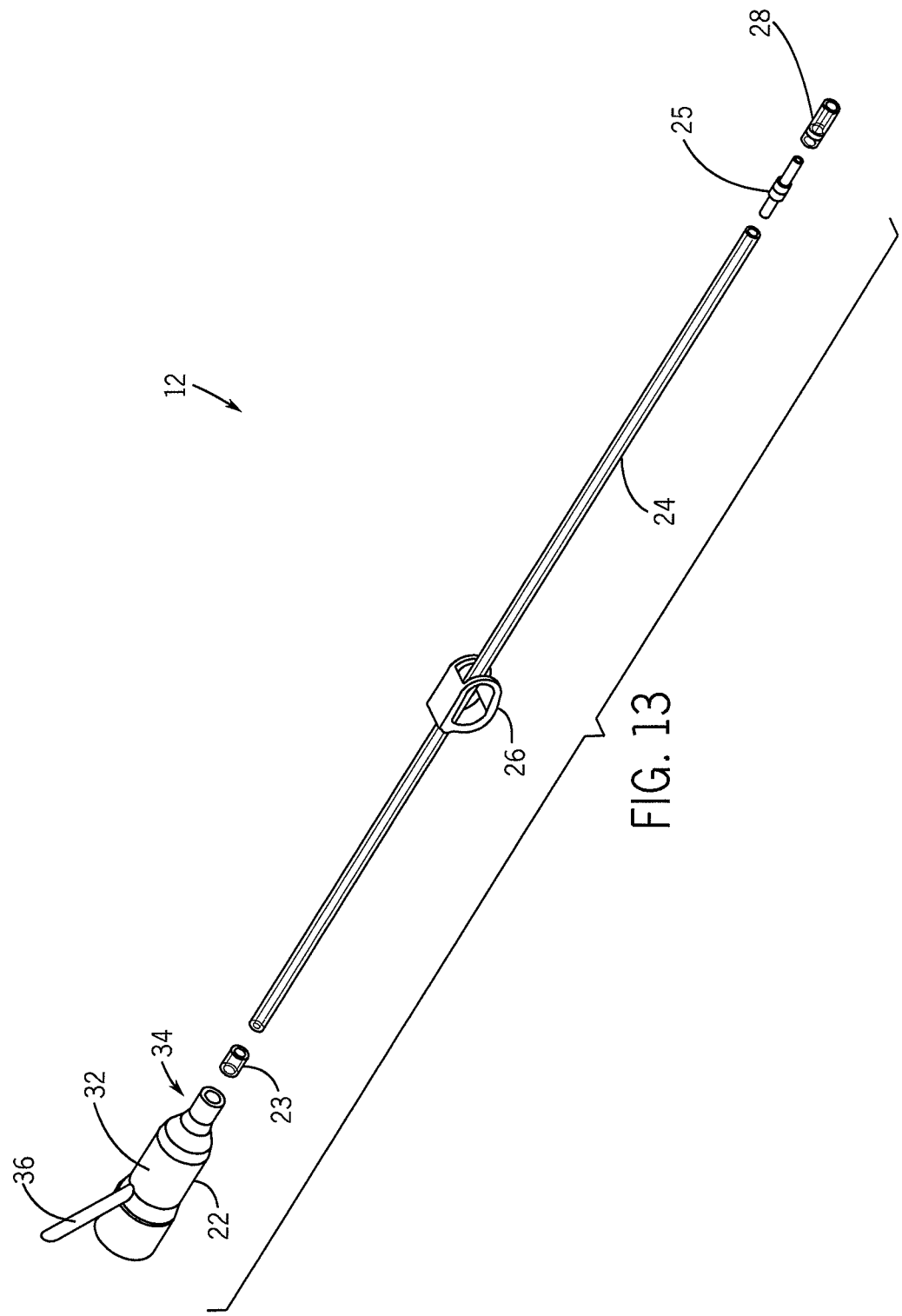
FIG. 13 is a perspective view, partially exploded, of a prior art IV Set commonly known as a Simplex IV Set.

As shown in FIGS. 2 and 13, a well known intravenous fluid administration set is commonly referred to as a Simplex IV Set. Simplex IV Sets are available from many sources including MAI of Spring Valley, Wis. USA or SyrVet of Waukee, Iowa USA. The Simplex IV Set 12 has a funnel assembly 22 which connects to the flange 20 and partially surrounds the neck 18 of the bottle 10 of solution, a length of flexible tubing 24, a flow regulating device such as a clamp 26 (for example a Halkey Roberts clamp)

connected to the tube 24, and a distal needle adapter 28 and needle 30. Connectors 23 and 25 may be used to connect the tubing 24 to the funnel 22 and adapter 25 respectively. The funnel 22 has a generally cylindrical body 32 which is communicatively connected to the hose 24 and a seal portion 34 disposed distally of the body 32 terminating in a distal aperture 35. The seal portion 34 has a diameter which is designed to mate with the bottle flange 20. The seal portion 34 may be tapered distally having a smaller diameter at the end, or may be have a non-tapered configuration so long as they have a diameter complementary for flexible mating over the lip 20 of the bottle 10. The funnel 22 has an air vent 36 for regulating pressure and release of air pockets or bubbles in the fluid flowing from the bottle 10 through the funnel 22 to provide smooth, continuous flow. The funnel 22 is typically made of flexible silicone based plastic material and is designed to stretch and fit over the flange or lip 20 of the bottle 10. However, funnels are also constructed of other materials such as natural or synthetic rubber. The inside diameter of the seal portion 34 of the funnel 22 is designed to be smaller than the lip diameter 20 with a taper above the seal portion 34 to assure a tight and fluid sealing fit. However, the overall arrangement of the bottle lip 20 with respect to the funnel 22 is essentially male to female during the connection or mating process. The Simplex IV Set 12 may be reusable or recyclable.

In the case of large animals such as cattle, IV fluid therapy may necessitate the use of several 500 ml bottles applied intravenously to each animal. And, often several animals are treated at the same time. The male to female connection of the bottle lip 20 to funnel 22 involving stretching the tapered flexible funnel 22 to the rigid or semi-rigid bottle lip 20 with a tight fit is a cumbersome. It is very difficult to maneuver the tapered seal portion 34 of the funnel 22 over the lip 20. This often results in spilling of fluids on the floor, apparatus, user, animal or all of the above. So at the very least it is a messy operation. Spillage is also costly in that expensive drugs, hydration fluids or nutrient fluid are wasted. Finally, the process of female over male flexible fitting is also very slow, resulting is wasted work time for the user 15. The process is difficult even under the best of circumstances. It becomes more difficult in very hot Summer conditions or very cold Winter conditions where the user may be sweating or wearing gloves. Veterinary or dairy/ranch users 15 are often distracted from the fine manual manipulation by the animal being under stress from the percutaneous puncture of the needle. Finally, all of this is exacerbated in large dairy or other animal operations where multiple animals are being treated.

Figure 6:
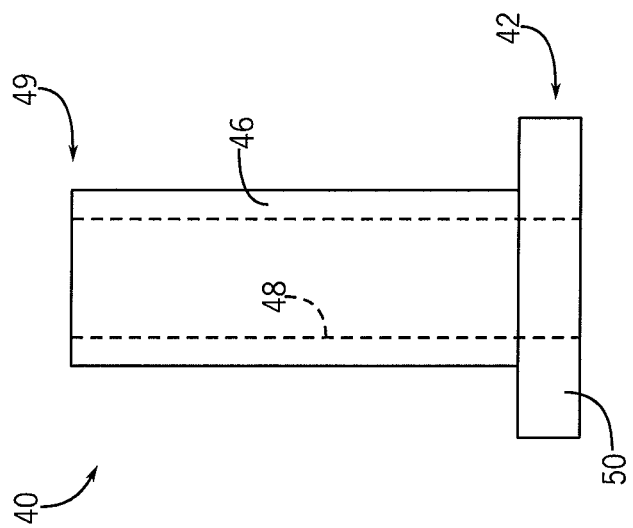
FIG. 6 is a side view of the adapter.
Figure 7:
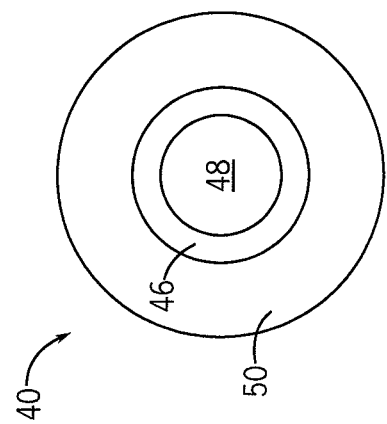
FIG. 7 is an end view of the adapter.
Figure 5:
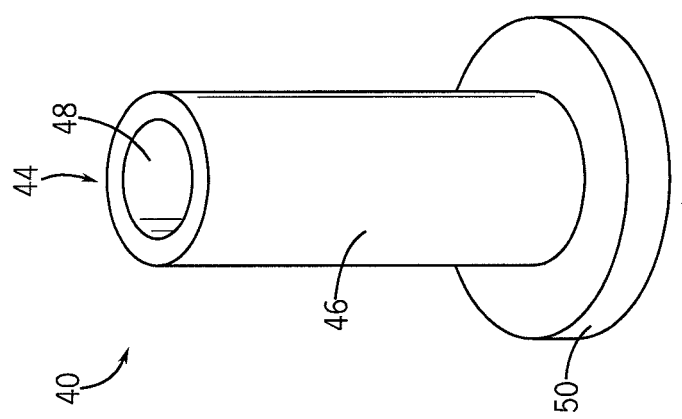
FIG. 5 is a perspective view of an embodiment of a quick connect adapter of the present invention.

The present invention provides an adapter which simplifies, sealingly facilitates, and speeds up the connection of and the interface between the Simplex IV Set 12 and the bottle 10. The invention also provides a method of using the adapter to easily, reliably and quickly connect the IV Set 12 and the bottle 10. Referring to FIGS. 5-7, one embodiment of the adapter 40 has a first end 42 for connection to a Simplex IV Set 12 and a second end 44 for connection to a bottle 10. The adapter 40 structure includes a cannular body portion 46 with a cylindrical configuration and a predetermined length and outside diameter. The body or cannulus 46 has an axial lumen 48 throughout its entire length, of a predetermined inside diameter. The adapter 40 also has a disk shaped lip portion 50 disposed at the second end 44 of the body 46. The lip 50 has a predetermined outside diameter which is greater than the outside diameter of the body 46, that complements the diameter of the funnel 22 for mating therewith. In use, the lip 50 forms a compression seal with the inside wall of the funnel 22 and the body 46 forms a compression seal with the bottle 10. The adapter 40 is preferably constructed of a rigid plastic such as butyl styrene, polypropylene or the like. The adapter 40 exterior may have some slight roughening to aid in forming a friction fit when mating with the funnel 22 and bottle 10. By way of a non-limiting example, in the embodiment shown in FIGS. 5-7, the adapter 40 has a length of 45.50 mm (1.79 inches) and the length of the body 46 is 40.00 mm (1.57 inches). The body 46 inside diameter (diameter of the lumen 48) is 10.88 mm (0.42 inch) and the outside diameter is 15.88 mm (0.62 inch). The diameter of the lip 50 is 29.00 mm (1.14 inch) and the thickness of the lip 50 is 5.50 mm.

Referring to FIGS. 8-12 an alternative embodiment of the adapter 60 also has a first end 62 for connection to a Simplex IV Set 12 and a second end 64 for connection to a bottle 10. The adapter 60 structure includes a tapered cannular body portion 66 with a tapered cylindrical configuration and a predetermined length and an outside diameter that is slightly smaller at its distal, second end 64. The body or cannulus 66 has an axial lumen 68 throughout its entire length, of a predetermined, tapering inside diameter. The adapter 60 also has a disk shaped lip portion 70 disposed at the second end 64 of the body 46. The lip 70 has a predetermined outside diameter which is greater than the outside diameter of the body 66. In use, the lip 70 forms a compression seal with the inside wall of the funnel 22 and the body 66 forms a compression seal with the bottle 10. The adapter 60 is preferably constructed of a rigid polymeric material. This tapered, male-type geometry facilitates mating of the second end 64 of the adapter 60 with the female-type aperture 21 of the bottle 10. In the embodiment shown in FIGS. 8-12, the adapter 60 has a length of 44.95 mm (1.77 inches) and the length of the body 66 is 39.62 mm (1.56 inches). The body 66 inside diameter (diameter of the lumen 68) is 11.55 mm (0.455 inch) at the distal, second end 64 and 12.70 mm (0.50 inch) at the first end 62. The outside diameter is 15.24 mm (0.60 inch) at the distal second end 64 and 16.25 mm (0.64 inch) at the first end 62. The diameter of the lip 70 is 28.70 mm (1.13 inch) and the thickness of the lip 70 is 0.21 inch.

Figure 3:
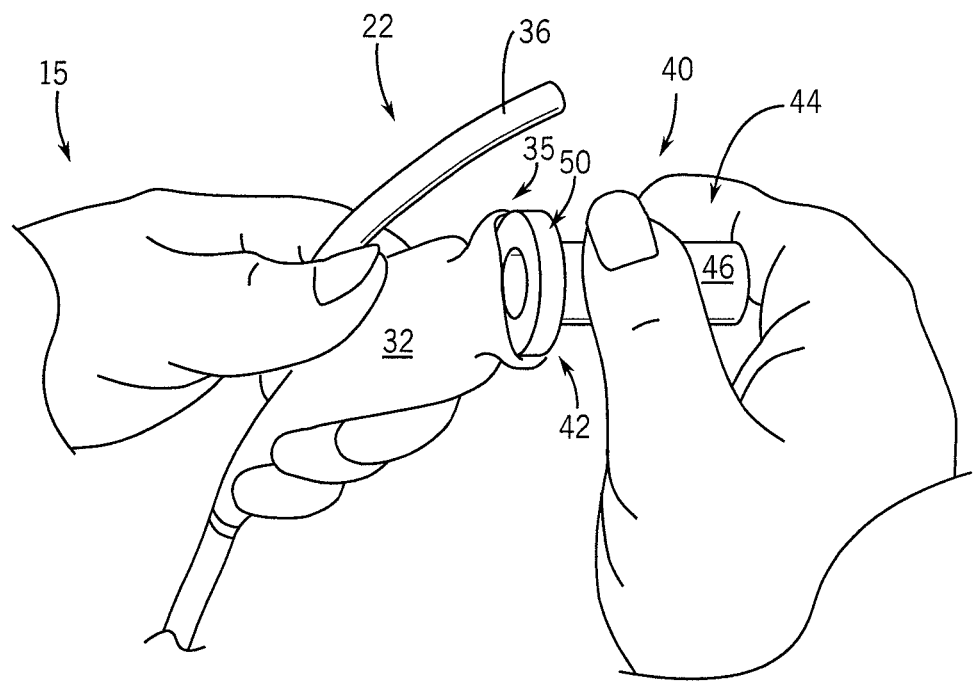
FIG. 3 illustrates a step in a method of the invention for connecting an IV set to a fluid bottle involving insertion of one end of an embodiment of interface apparatus of the present invention into the funnel of the IV set.
Figure 4:
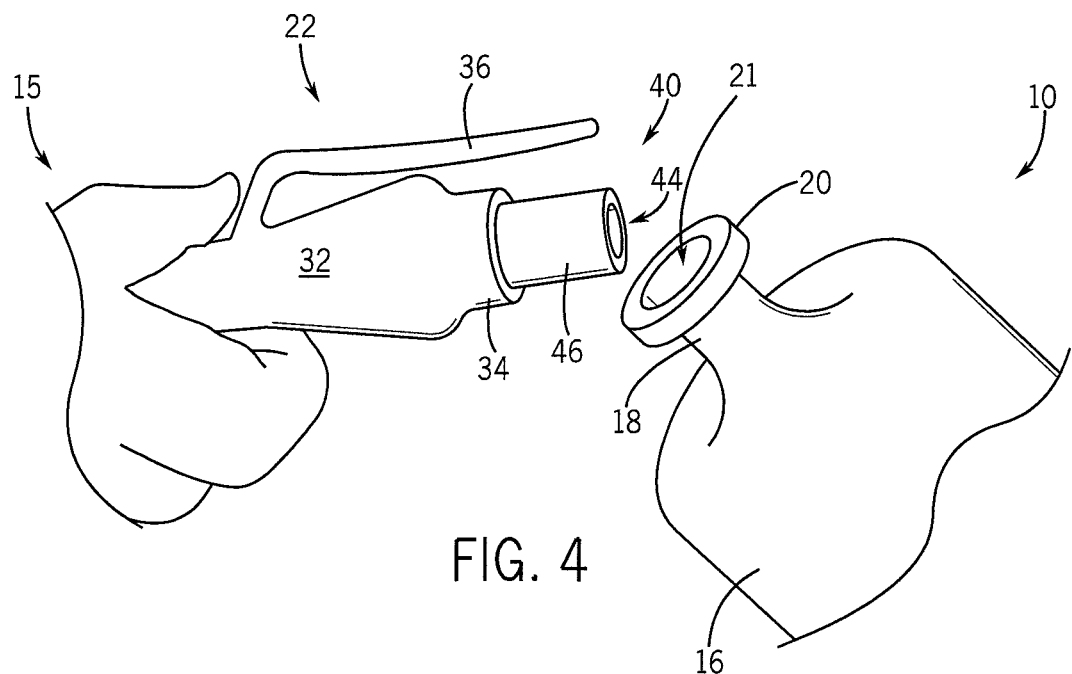
FIG. 4 illustrates a further step in the method of the invention involving insertion of the other end of the interface apparatus into a fluid bottle.

Referring to FIGS. 3 and 4, a preferred embodiment of the method of quickly, accurately and repeatably connecting the IV Set 12 to the bottle 10 involves first providing an interface means such as adapter 40 or adapter 60. Then coupling the adapter 40 with the funnel 22 in a semipermanent fashion by inserting first end 42 of the adapter 40 into the funnel 22, whereby the lip 50 passes into the aperture 35 of the funnel 22 and extends just short of the air vent 36. The seal end 34 surrounds the adapter lip 50 creating a fluid tight seal. The lip portion 50 will register and align just above the air vent 36. This will provide a semipermanent seal between the adapter 40 and the funnel 22, leaving the cannular portion 46 exposed outside the funnel 22. Next, a bottle 10 is obtained by the user 15 and its end cap or seal removed to expose the aperture 21. The second end 44 of the adapter 40 is then inserted into the bottle 10, whereby the cannular portion 46 is inserted into the opening of the bottle 10 until a tight seal is formed. The bottle 10 can then be inverted and held a loft by the user 15 or other support means for fluid to flow from the bottle 10 and into the I.V. set 12. When the bottle 10 is emptied, the funnel 22 is grasped by the user 15 and retracted from the bottle aperture 21. The empty bottle 10 is discarded and a new bottle 10 is obtained. After removing the cap or seal of the new bottle 10 the fluid egress aperture 21 is exposed. The second end 44 of the funnel 22 is inserted into the aperture 21 and slight pressure is exerted until a firm fit and fluid seal is established. The new bottle 10 is then inverted to continue or re-establish fluid flow through the Simplex IV Set 12. The process can be repeated as many times as necessary. After completion of IV Therapy, the adapter 40 may be discarded or cleaned and stored for reuse.

The invention provides an adapter apparatus and a method of use therefore which efficiently and quickly transfers a Simplex IV Set 12 from one bottle 10 of veterinary medical fluid (medicament, hydration, and/or nutrient solutions) to a second bottle during the IV Fluid Therapy for animals such as cattle, horses and the like. In summary, a first end 42 of the adapter 40 is insertable into the distal aperture 35 (female-type portion) of a Simplex IV Set Funnel 22. The second end 44 of the adapter 40 protrudes from the funnel 22 and is easily seen and manipulated by the user 15. The second end 44 is insertable into the egress aperture 21 (female-type portion) of a IV Fluid bottle 10. Both ends 42 and 44 form a fluid tight seal with the funnel 22 and bottle 10 apertures 35 and 21 respectively. The second end 44 is preferably tapered to make insertion easier, to adapt to a range of sizes of bottle neck apertures 21, and to yield a friction fit that is easy to establish and hold and at the same time to disconnect, and which provides a reliable fluid seal. The second end 44 of the adapter 40 is quickly disconnectable from the bottle 10 upon being emptied of fluid. The second end 44 can then be inserted into a new full bottle 10 of fluid. The adapter and method of use obviates the need to stretch and friction fit the Simplex Funnel 22 over the outside of the bottle lip/mouth 20 in the old female over male arrangement of the prior art. One adapter adapts to a range bottle neck sizes ranging from 28-33 mm. And the adapter 40 is attachable to either a rubber or plastic type Simplex funnel. In summary, the adapter and method provide a quick, easy transfer of bottles to a Simplex IV set 12, little or no interruption of fluid flow occurs, little or no spilling of fluid occurs, less stress of the animal 14 occurs, and the user 15 can accomplish more work faster with less frustration.

Although the apparatus and method of the invention has been described and shown in terms of separate and independent adapter structures such as devices 40 and 60, it is within the purview of the invention that the Simplex IV Set could be modified to include the adapter features in a permanent arrangement to yield a male-type funnel with a cannulus for male-type mating with female-type bottle apertures.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. A veterinary medical method for rapidly changing bottles of fluids used in intravenous (IV) fluid therapy for large animals selected from the group consisting of cattle, horses, pigs and goats, comprising:
   (a) providing at least two bottles of large animal IV fluid, each bottle having a capacity of at least 500 ml., each bottle having an open, female-type fluid egress aperture with a predetermined inside diameter;
   (b) providing a flexible IV set including a funnel having a flexible body with a female-type connection aperture, the funnel being constructed of elastic material, a flexible fluid flow tube communicatively connected to the funnel, and an IV needle communicatively connected to the tube and adapted for intravenous coupling with a large animal;
   (c) providing an adapter apparatus comprising a cylindrical cannular portion with two ends, one end having a predetermined outside diameter that is equivalent to the inside diameter of the bottle and being adapted for male-type sealing mating with the female-type fluid egress aperture of the fluid bottle and the other end having a lip portion adapted for male-type sealing mating with the female-type funnel connection aperture of the flexible IV set funnel;
   (d) coupling the adapter apparatus in a semi-permanent fashion to the IV set funnel by inserting the male-type lip portion of the adapter apparatus into the female-type funnel connection aperture of the IV set funnel and flexibly female-type moving the elastomeric funnel over the male-type lip portion of the adapter apparatus;
   (e) inserting the male-type cannular portion of the adapter apparatus into the female-type fluid egress aperture of the fluid bottle;
   (f) inverting the fluid bottle to facilitate the flow of fluid from the bottle, through the adapter apparatus and into the IV set, and
   (g) rapidly changing the bottles by retracting the cannular portion of the adapter from the first fluid bottle and inserting the cannular portion into the second fluid bottle, both bottles being unobstructed at the fluid egress aperture with no membrane.

2. The method of claim 1 further comprising the step of regulating flow of fluid in the I.V. set.

3. A rapid IV bottle exchange adapter for use in IV Therapy for large animals selected from the group consisting of cattle, horses, pigs and goats for connecting a large animal IV Set to a 500 ml. bottle containing large animal IV fluid, the IV Set being of the type having a flexible funnel with a female-type connection aperture, consisting of
   a generally cylindrical body with a fluid flow lumen, the body having a lip disposed at one end adapted for male-type connection to the IV Set female-type connection aperture, the opposing end of the body being adapted for male-type insertion into the female-type fluid egress aperture of the bottle,
   wherein the lip has a disc shaped configuration with a cylindrical peripheral surface having a diameter of 29 mm, which is greater than the diameter of the cylindrical body;
   wherein the body has a predetermined length of 40 mm
   wherein the body has a tapered outside diameter, the body tapering smaller from the lip to a terminal end from 16.25 mm to 15.24 mm
   wherein the inside diameter tapers from one end to the other end of the adapter from 12.70 mm. to 11.55 mm.

4. The adapter of claim 3, wherein adapter is constructed of a plastic material.

5. An apparatus for administering intravenous (IV) fluid therapy to large animals selected from the group consisting of cattle, horses, pigs and goats, rapid IV bottle exchange, comprising:
   (a) a plurality of 500 ml. bottles of IV fluid, each bottle having an open fluid egress aperture;
   (b) an IV Set including a flexible, stretchable funnel with a female-type connection aperture, a flexible fluid flow tube communicatively connected to the funnel, and an IV needle communicatively connected to the tube and adapted for intravenous coupling with a large animal; and
   (c) an adapter for connecting the Simplex IV Set to one of the bottles containing fluid, the adapter comprising a generally cylindrical body with a fluid flow lumen, the body having a lip disposed at one end adapted for male-type connection to the IV Set female-type connection aperture, the opposing end of the body being adapted for male-type insertion into the female type fluid egress aperture of the bottle, wherein (1) the lip has a disc shaped configuration with a cylindrical peripheral surface having a diameter which is greater than the diameter of the cylindrical body, (2) wherein the body has a predetermined length, outside diameter, and inside lumen diameter, wherein:
   i. the lip outside diameter is 29 mm and the body has a tapered outside diameter, the body tapering smaller from the lip to a terminal end from 16.25 mm to 15.24 mm
   ii. the inside diameter tapers from the lip end to the terminal end of the adapter from 12.70 mm. to 11.55 mm; and
   iii. the length of the body is 40 mm.

* * * * *